United States Patent
Yoon et al.

[11] Patent Number: 6,101,404
[45] Date of Patent: Aug. 8, 2000

[54] OPTICAL DIAGNOSIS POINT DETECTOR FOR NONINVASIVE DIAGNOSIS OF BLOOD CONSTITUENTS AND NONINVASIVE DIAGNOSTIC DEVICE

[75] Inventors: Gil-won Yoon, Sungnam; Sang-min Lee, Seoul; Hong-sig Kim, Seoul; Won-ky Kim, Seoul, all of Rep. of Korea

[73] Assignee: Samsung Electronics Co., Ltd., Kyungki, Rep. of Korea

[21] Appl. No.: 08/862,264

[22] Filed: May 23, 1997

[30] Foreign Application Priority Data

May 23, 1996 [KR] Rep. of Korea .................... 96-17732

[51] Int. Cl.[7] ................................................ A61B 5/00
[52] U.S. Cl. .................. 600/310; 600/309; 600/322; 600/504
[58] Field of Search ......................... 600/309, 310, 600/322, 323, 336, 340, 453, 454, 465, 473, 476, 479, 485, 500, 504

[56] References Cited

U.S. PATENT DOCUMENTS

| | | | |
|---|---|---|---|
| 4,830,017 | 5/1989 | Perry et al. | 600/500 |
| 5,273,046 | 12/1993 | Butterfield et al. | 600/500 |
| 5,370,114 | 12/1994 | Wong et al. | |
| 5,800,348 | 9/1998 | Kaestle | 600/336 |
| 5,832,924 | 11/1998 | Archibald et al. | |

FOREIGN PATENT DOCUMENTS

| | | |
|---|---|---|
| 0426358 | 5/1991 | European Pat. Off. |
| 0587009 | 3/1994 | European Pat. Off. |

*Primary Examiner*—Linda C. M. Dvorak
*Assistant Examiner*—Bryan K. Yarnell
*Attorney, Agent, or Firm*—Kile, McIntyre, Harbin & Lee; Eugene M. Lee

[57] ABSTRACT

An optimal diagnosis point detector for noninvasive diagnosis of blood constituents and a noninvasive diagnosis device using the same. The optimal diagnosis point detector for noninvasive diagnosis of blood constituents includes detecting means for detecting a predetermined signal concerning bloodstream quantity from a portion of a subject to be diagnosed, driving means for driving the detecting means, amplifying means for amplifying the output signal of the detecting means, analog-to-digital (A/D) converting means for receiving the signal output from the amplifying means and converting the same into digital data, storage means for storing a predetermined optimal diagnosis point detecting method, means through which a user's command is input, central processing means, connected to the driving means, the A/D converting means, the command inputting means, and the storage means, for performing the predetermined optimal diagnosis point detecting method stored in the storage means according to the user's input command, and display means connected to the central processing means for displaying a detected value and displaying an indication that the detected value is the maximum value when a maximum detection signal is detected from the detecting means. Therefore, the concentration of blood constituents of a subject to be diagnosed can be calculated accurately. Also, the constituents that are very lightly concentrated in the blood can be accurately measured.

23 Claims, 8 Drawing Sheets

OPTICAL DIAGNOSIS POINT DETECTOR FOR NONINVASIVE DIAGNOSIS OF BLOOD CONSTITUENTS AND NONINVASIVE DIAGNOSTIC DEVICE

BACKGROUND OF THE INVENTION

The present invention relates to a noninvasive diagnostic device, and more particularly, to an optimal diagnosis point detector for noninvasive diagnosis of blood constituents for detecting an optimal diagnosis point among various portions of a subject's body, and a noninvasive diagnostic device for performing a noninvasive diagnosis at the detected point using the same.

In general, a noninvasive diagnostic device irradiates light of a specific wavelength into a predetermined portion of the body, such as fingers or a wrinkle, and detects the light reflected or transmitted from the light-irradiated portion, thereby measuring the concentration of blood constituents such as hemoglobin, glucose, cholesterol, alcohol or villirubin. In other words, light of a specific wavelength, a wavelength at which the light reacts readily with a specific blood constituent and a large quantity of light is absorbed, is irradiated into a diagnosis portion to detect reflected or transmitted light. Then, the light which is absorbed less readily is irradiated into the specific diagnostic portion to detect reflected or transmitted light. Finally, the concentration of blood constituents is calculated using experimentally precalculated data of the concentration and absorbance of a specific constituent by means of the amount of two kinds of the detected light.

However, in the case of using a conventional noninvasive diagnostic device, since a user does not detect a diagnostic portion having the maximum detected value due to a high flow of blood in a bloodstream to be measured, the reflected or transmitted light amount is very small, which makes it difficult to measure blood constituents accurately. In other words, the constituents that are heavily concentrated in the blood can be measured to some extent, but the measurement accuracy is poor. Further, the constituents that are lightly concentrated in the blood are difficult to measure.

SUMMARY OF THE INVENTION

It is an object of the present invention to provide an optimal diagnosis point detector for noninvasive diagnosis of blood constituents that detects a point having the maximum detected value due to a high flow of blood in a bloodstream among various diagnosis portions of a subject.

Another object of the present invention is to provide a noninvasive diagnostic device using an optimal diagnosis point detector for noninvasive diagnosis of blood constituents that accurately measure the concentration of a subject's blood constituents by detecting a point at which a detected value is largest using an optimal diagnosis point detector for noninvasive diagnosis of blood constituents and by performing the noninvasive diagnosis at the detected point.

To accomplish the first object of the present invention, an optimal diagnosis point detector for noninvasive diagnosis of blood constituents comprises: detecting means for detecting a predetermined signal concerning bloodstream quantity from a portion of a subject to be diagnosed; driving means for driving the detecting means; amplifying means for amplifying the output signal of the detecting means; analog-to-digital (A/D) converting means for receiving the signal output from the amplifying means and converting the same into digital data; storage means for storing a predetermined optimal diagnosis point detecting method; means through which a user's command is input; central processing means connected to the driving means, the A/D converting means, the command inputting means and the storage means, for performing the predetermined optimal diagnosis point detecting method stored in the storage means according to the user's input command; and display means connected to the central processing means for displaying a detected value and displaying an indication that the detected value is the maximum value when a maximum detection signal is detected from the detecting means.

In a preferred embodiment, the optimal diagnosis point detecting method performed by the central processing means comprises: a) operating the driving means by applying a predetermined signal thereto; b) converting the signal amplified by the amplifying means after being detected from the detecting means operated by the output signal of the driving means into digital data using the A/D converter; c) comparing the digital data value with a predetermined reference value, moving a detection point, and then returning the operation to the step b) if the digital data value is smaller than the predetermined reference value, and proceeding to a subsequent step if the digital data value is greater than or equal to the predetermined reference value; and d) displaying the digital data value on the display means and displaying an indication that the digital data value is a maximum value.

Also, in a preferred embodiment, the optimal diagnosis point detecting method performed by the central processing means comprises: a) operating the driving means by applying a predetermined signal thereto; b) converting the signal amplified by the amplifying means after being detected from the detecting means operated by the output signal of the driving means into digital data using the A/D converter; c) comparing the digital data value with a predetermined reference value, moving a detection point, and then returning the operation to the step b) if the digital data value is smaller than the predetermined reference value, and proceeding to a subsequent step if the digital data value is greater than or equal to the predetermined reference value; d) replacing the reference value with the value of the digital data; e) displaying the digital data value on the display means; f) determining whether the number of detections is greater than or equal to a predetermined number of times, moving a detection point, and then returning the operation to the step b) if the number of detections is smaller than the predetermined number, and proceeding to a subsequent step if the number of detections is greater than or equal to the predetermined number; and g) displaying the reference value on the display means and displaying an indication that the reference value is a maximum value.

Also, a preferred embodiment of the invention also may include means for filtering the output of the amplifying means between the amplifying means and the A/D converter.

Further, it is preferred that the detecting means includes light generating means for generating light to irradiate the light into the portion to be diagnosed, and a photodetector means for detecting the light amount reflected or transmitted from the portion to be diagnosed.

The light generating means is preferably any one of a flash lamp for generating pulsating light and a continuous emitting bulb.

Also, it is preferred that the detecting means includes an ultrasonic generating means for generating an ultrasonic wave to irradiate the wave into the portion to be diagnosed and an ultrasonic detecting means for detecting the frequency of the ultrasonic wave reflected from the portion to be diagnosed.

Also, it is preferred that the detecting means is a piezoelectric element for detecting variations in pressure of the portion to be diagnosed, which changes according to the flow of the bloodstream.

Further, it is preferred that the detecting means is a charge-coupled device (CCD) camera, and the optimal diagnosis point detecting method is performed by photographing the portion to be diagnosed with the CCD camera and then detecting the portion where the level of brightness in the grade scale changes sharply due to a large flow of blood in a bloodstream at the photographed portion.

To accomplish the second object of the present invention, an noninvasive diagnostic device comprises: first detecting means for detecting a predetermined signal concerning bloodstream quantity from a portion of a subject to be diagnosed; first driving means for driving the first detecting means; first amplifying means for amplifying the output signal of the first detecting means; first light emitting means for generating a plurality of beams having different wavelengths to react to blood constituents to be measured to irradiate the beams into the portion to be diagnosed; second light emitting means for generating a plurality of beams having different wavelengths to react to the constituents other than the blood constituents to be measured to irradiate the beams into the portion to be diagnosed; second detecting means for detecting the reflected or transmitted light from the portion to be diagnosed after the beams from the first and second light emitting means are irradiated; second driving means for driving the first light emitting means; third driving means for driving the second light emitting means; first filtering means having a plurality of filters for filtering the respective outputs of the second detecting means at frequency bands of the respective beams generated by the first light emitting means; second filtering means having a plurality of filters for filtering the respective outputs of the second detecting means at frequency bands of the respective beams generated by the second light emitting means; second amplifying means having a plurality of amplifiers for amplifying the respective outputs of the first filtering means; third amplifying means having a plurality of amplifiers for amplifying the respective outputs of the second filtering means; multiplexing means for multiplexing the outputs of the first, second, and third amplifying means; analog-to-digital (A/D) converting means for converting the output signal of the multiplexing means into digital data; storage means for storing a predetermined optimal diagnosis point detecting method and a blood constituent concentration calculating method; command inputting means through which a user's command is input; central processing means connected to the first, second, and third driving means, the A/D converting means, the storage means, and the command inputting means for performing the optimal diagnosis point detecting method and the blood constituent concentration calculating method stored in the storage means according to the user's input command; and display means connected to the central processing means for displaying a detected value, displaying an indication that the detected value is the maximum value when a maximum detection signal is detected from the first detecting means, and displaying the calculated blood constituent concentration.

It is preferred that the optimal diagnosis point detecting method and the blood constituent concentration calculating method performed by the central processing means comprise: a) operating the first driving means by applying a predetermined signal thereto; b) converting the signal amplified by the first amplifying means after being detected from the first detecting means operated by the output signal of the first driving means into digital data using the A/D converter by applying a control signal to the multiplexing means and inputting the same into the A/D converting means; c) comparing the digital data value with a predetermined reference value, moving a detection point, and then returning the operation to the step b) if the digital data value is smaller than the predetermined reference value, and proceeding to a subsequent step if the digital data value is greater than or equal to the predetermined reference value; d) displaying the digital data value on the display means and displaying an indication that the digital data value is the maximum value; e) operating the second driving means by applying a predetermined signal thereto when the optimal diagnosis point is detected by steps a) through d); f) inputting a plurality of signals amplified by the second amplifying means after being detected from the second detecting means and filtered by the first filtering means into the A/D converting means by applying a control signal into the multiplexing means, converting the same into digital data, and storing the converted data in the storage means; g) inputting a plurality of signals amplified by the third amplifying means after being detected from the second detecting means and filtered by the second filtering means into the A/D converting means by applying a control signal into the multiplexing means, converting the same into digital data, and storing the converted data in the storage means; h) calculating the amount of noise components other than the components to be measured using the value converted into digital data via the second filtering means; i) eliminating the noise components from the data of blood constituents to be measured by subtracting a value obtained by reflecting a scale constant on the noise component amount calculated in step h) from the converted value via the first filtering means; j) calculating the concentration of blood constituents to be measured using the value of the noise-eliminated blood constituents; and k) displaying the calculated concentration on the display means.

In another preferred embodiment, the optimal diagnosis point detecting method and the blood constituent concentration calculating method performed by the central processing means comprise: a) operating the first driving means by applying a predetermined signal thereto; b) converting the signal amplified by the first amplifying means after being detected from the first detecting means into digital data using the A/D converter by applying a control signal to the multiplexing means and inputting the same into the A/D converting means; c) comparing the digital data value with a predetermined reference value, moving a detection point, and then returning the operation to step b) if the digital data value is smaller than the predetermined reference value, and proceeding to a subsequent step if the digital data value is greater than or equal to the predetermined reference value; d) replacing the reference value with a value of the digital data; e) displaying the reference value on the display means; f) determining whether the number of detections is greater than or equal to a predetermined number, moving a detection point, and then returning the operation to step b) if the number of detections is smaller than the predetermined number, and proceeding to a subsequent step if the number of detections is greater than or equal to the predetermined number; g) displaying the reference value and displaying an indication that the reference value is the maximum value; h) operating the second driving means by applying a predetermined signal thereto when the optimal diagnosis point is detected by steps b) through g) ; i) sequentially inputting a plurality of signals amplified by the second amplifying means after being detected from the second detecting means and filtered by the first filtering means into the A/D converting means by applying a control signal into the multiplexing means, converting the same into digital data, and storing the converted data in the storage means; j) inputting a plurality of signals amplified by the third amplifying means after being detected from the second detecting means and filtered by the second filtering means into the A/D converting means by applying a control signal into the A/D converting means, converting the same into digital data, and storing the converted data in the storage means; k) calculating the amount of noise components other than the components to be measured using the value converted into digital data via the second filtering means; l) eliminating the noise components from the data of blood constituents to be measured by subtracting a value obtained by reflecting a scale constant on the noise component amount calculated in the step k) from the converted value via the first filtering means; m) calculating the concentration of blood constituents to be measured using the value of the noise-eliminated blood constituents; and n) displaying the calculated concentration on the display means.

Further, it is preferred that the first detecting means comprises light generating means for generating light to irradiate the light into the portion to be diagnosed, and a photodetector means for detecting the light amount reflected or transmitted from the portion to be diagnosed.

Also, it is preferred that the light generating means is any one of a flash lamp for generating pulsating light and a continuous emitting bulb.

It is preferred that the first and second light emitting means are any one of a laser diode and an emitting diode, and a lamp for generating the light of a wide-band frequency.

Further, it is preferred that the first and second light emitting means are any of a flash lamp for generating pulsating light and a continuous emitting bulb for emitting continuous light.

BRIEF DESCRIPTION OF THE DRAWINGS

The above objects and advantages of the present invention will become more apparent by describing in detail preferred embodiments thereof with reference to the attached drawings in which.

DETAILED DESCRIPTION OF THE PREFERRED EMBODIMENTS

Hereinbelow, various embodiments of the present invention will now be described with reference to accompanying drawings.

Figure 1:
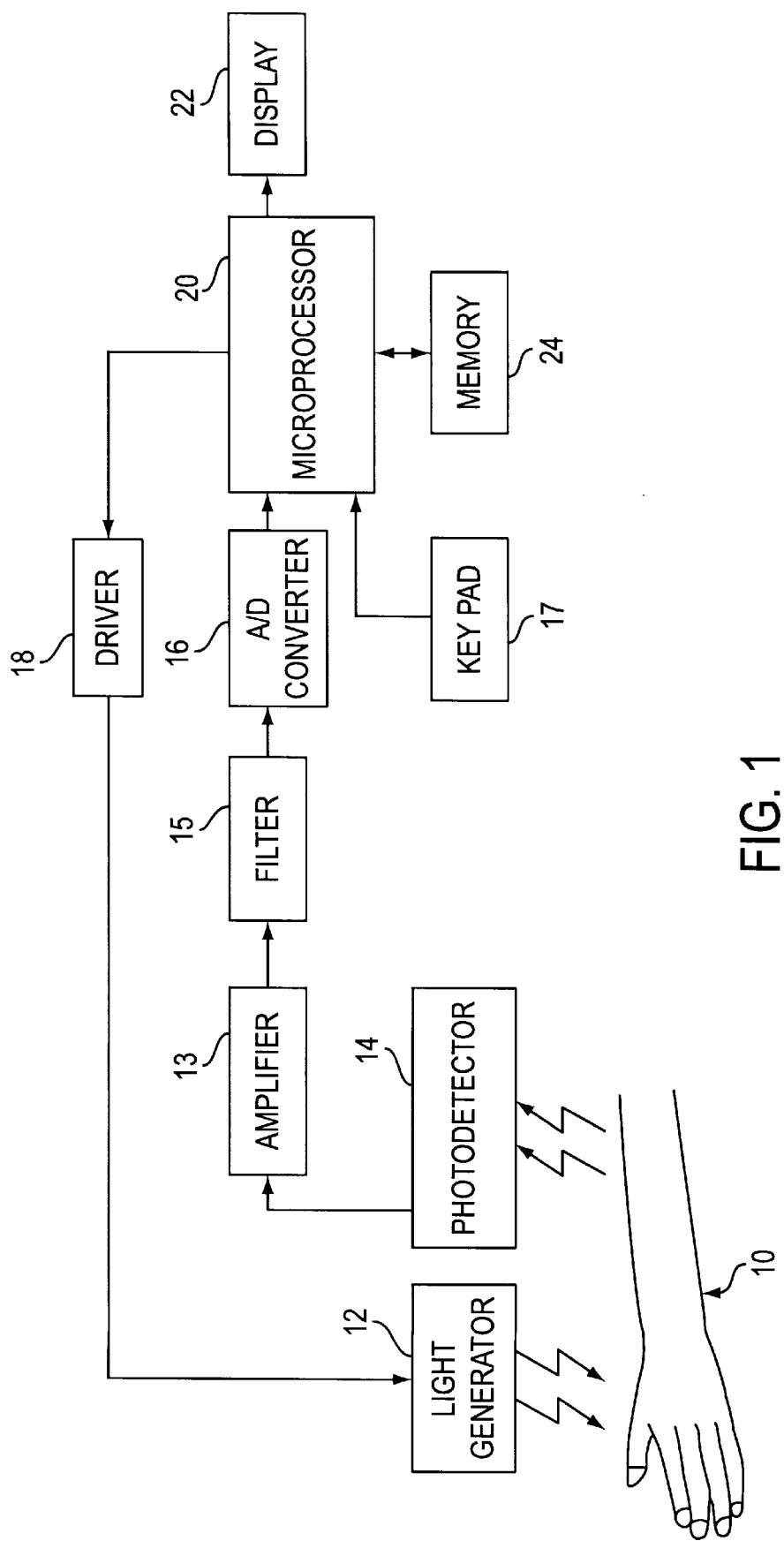
FIG. 1 is a block diagram illustrating an optimal diagnosis point detector for noninvasive diagnosis of blood constituents according to a first embodiment of the present invention.

Referring to FIG. 1, the optimal diagnosis point detector for noninvasive diagnosis of blood constituents according to a first embodiment of the present invention includes a light generator 12 for irradiating light of a predetermined wavelength into a portion 10 of the subject to be diagnosed, a photodetector 14 for detecting the amount of light that is reflected from the subject's blood constituents, a driver 18 for driving the light generator 14, an amplifier 13 for amplifying the detection signal output from the photodetector 14, a filter 15 for filtering the output signal of the amplifier 13, an analog-to-digital (A/D) converter 16 for receiving the signal output from the filter 15 and converting the same into digital data, a memory 24 in which a predetermined optimal diagnosis point detecting method is stored, a key pad 17 through which a user's command is input, a microprocessor 20 connected to the driver 18, the A/D converter 16, the key pad 17, and the memory 24, for performing the optimal diagnosis point detecting method stored in the memory 24 according to the user's input command, and a display 22, connected to the microprocessor 20, for displaying the detected value and displaying that the detected value is the maximum value when the maximum detection signal is detected from the photodetector 14.

The operation of the above optimal diagnosis point detector for noninvasive diagnosis of blood constituents according to a first embodiment of the present invention will now be explained with reference to FIG. 5, in view of the optimal diagnosis point detecting method performed by the microprocessor 20.

Figure 5:
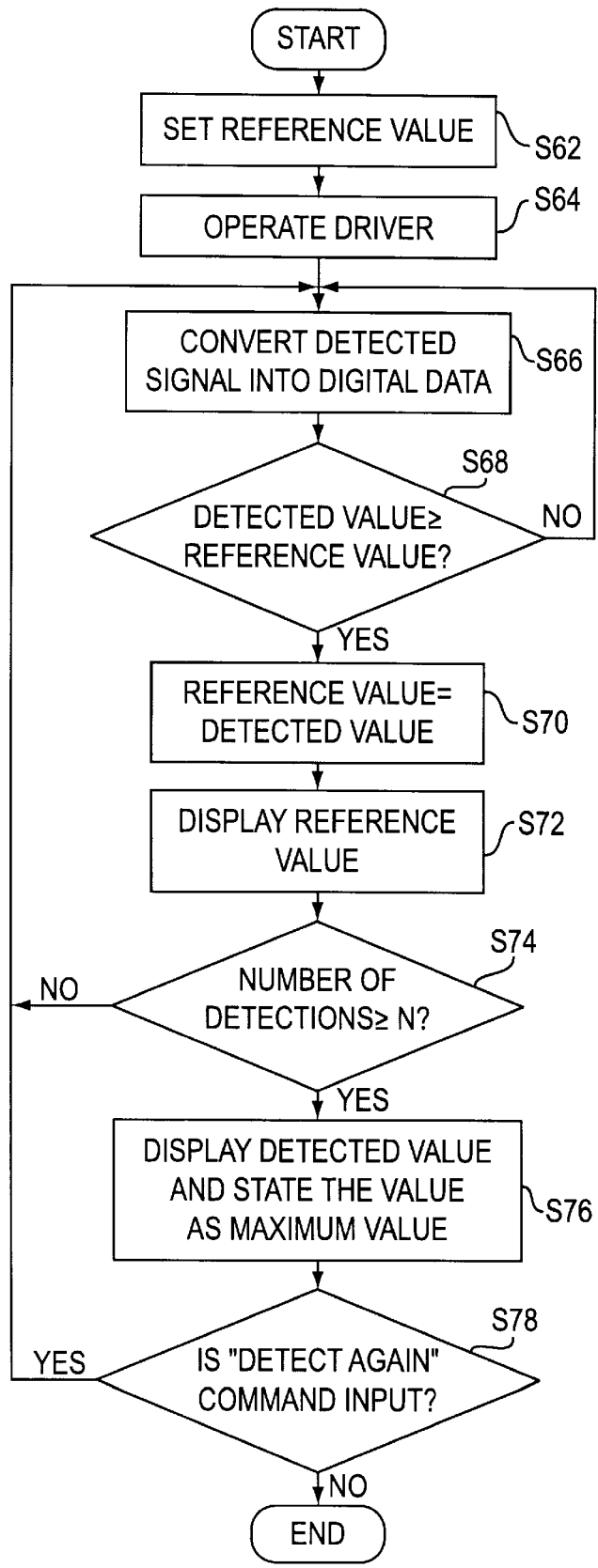
FIG. 5 is a flow chart for explaining the operation of the optimal diagnosis point detector for noninvasive diagnosis of blood constituents shown in FIG. 1.

Referring to FIGS. 1 and 5, when a "Start" command is input through the key pad 17 by a user, the microprocessor 20 sets a predetermined reference value in step S62. In step S64, a predetermined signal is applied to the driver 18 to drive the same. If the driver 18 is operated, the light generator 12 generates light of a predetermined wavelength to irradiate the light into the portion 10 to be diagnosed. Here, the light generator 12 is preferably a flash lamp for generating pulsating light of a predetermined width or a continuous emitting bulb for emitting continuous light. Specifically, if the flash lamp is used as the light generator 12, the light generator 12 generates very strong light pulses instantaneously. Thus, a signal-to-noise ratio is improved, thereby enhancing the overall performance. Among the light beams irradiated into the portion 10 to be diagnosed, the reflected light is detected in the photodetector 14, amplified in the amplifier 13, and is filtered by the filter 15. In step S66, this filtered signal is converted into digital data by the A/D converter 16. In step S68, the converted digital data, i.e., the detected value, and a predetermined reference value are compared. If the detected value is smaller than the predetermined reference value, the detection point is moved, and the operation returns to the step S66. If the detected value is greater than or equal to the reference value, the operation proceeds to a subsequent step. In step S70, the reference value is replaced with the detected value. In step S72, the reference value replaced with the detected value is displayed on the display 22. In step S74, a determination of whether the number of detections is greater than or equal to a predetermined number of times (N) is made. If the number of detections is less than N, the detection point is moved, and the operation returns to step S66. If the number of detection is greater than or equal to N, the operation proceeds to a subsequent step. In step S76, the reference value replaced with the detected value is displayed on the display 22, and an indication that the reference value is the maximum value is displayed. In step S78, a determination of whether a "Detect Again" command has been input is made. If "Detect Again" is input, the operation returns to step S66; otherwise, the optimal diagnosis point detecting method is complete.

To reposition the photodetector 14 at a point where the detected value is the largest, steps S66 and S68 are repeatedly performed until a value greater than or equal to the maximum detected value is detected while the detected points are detected again by moving the light generator 12 and photodetector 14. When the maximum value is displayed again on the display 22, the detection is terminated.

Figure 6:
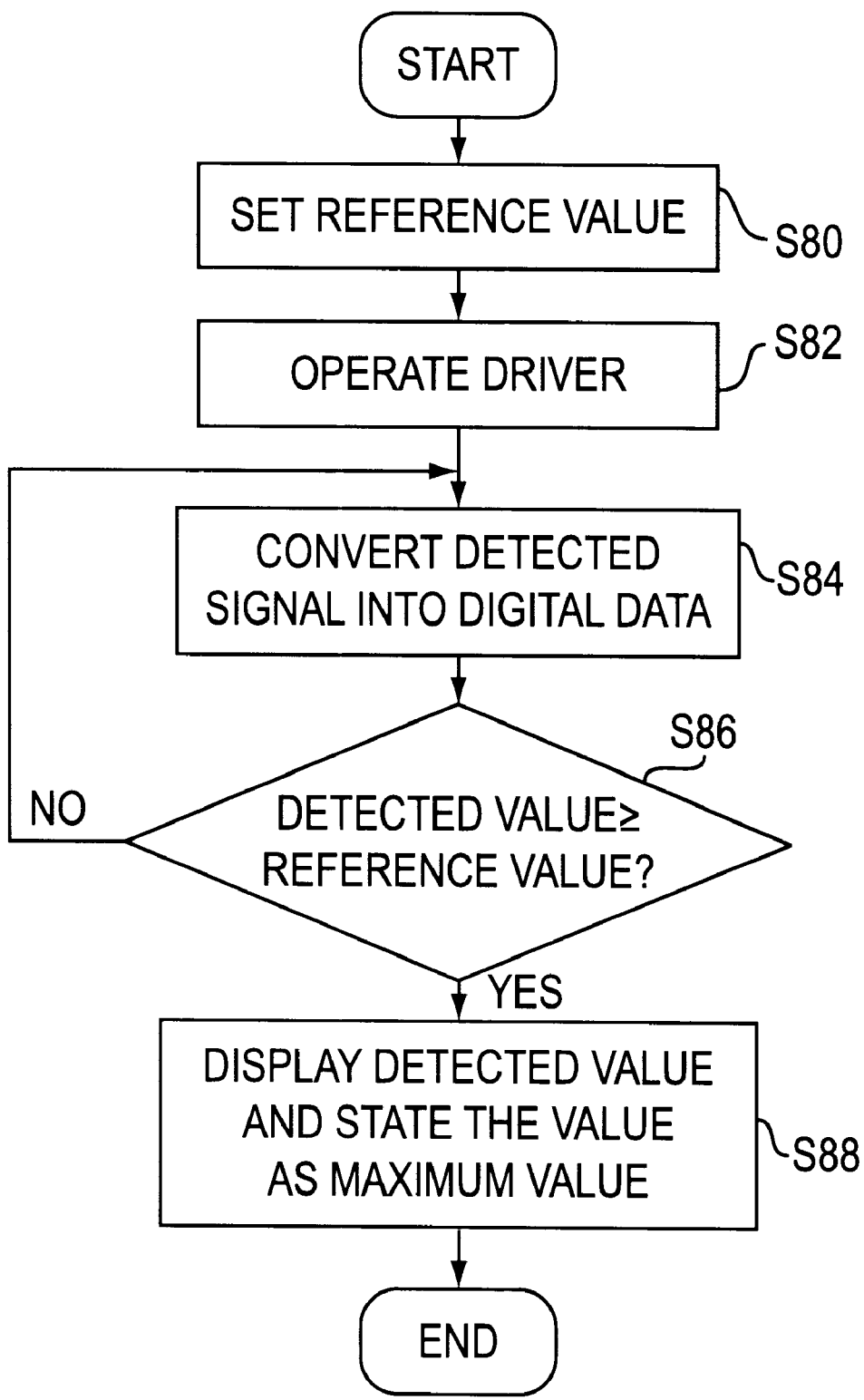
FIG. 6 is another flow chart for explaining the operation of the optimal diagnosis point detector for noninvasive diagnosis of blood constituents shown in FIG. 1.

FIG. 6 shows another optimal diagnosis point detecting method, in which the optimal diagnosis point is detected by determining a point where the detected value is greater than or equal to a predetermined reference value to be the optimal diagnosis point. Here, the reference value is a value obtained experimentally for accurate calculation of blood constituents.

Referring to FIGS. 1 and 6, if a "Start" command is input through the key pad 17, the microprocessor 20 sets a predetermined reference value is step S80. In step S82, a predetermined signal is applied to the driver 18 to operate the driver 18. If the driver 18 is operated, the light generator 12 generates light of a predetermined wavelength to irradiate the light into the portion 10 to be diagnosed. Among the light beams irradiated into the portion 10 to be diagnosed, the reflected light is detected in the photodetector 14, amplified in the amplifier 13, and is filtered by the filter 15. In step S84, this filtered signal is converted into digital data by the A/D converter 16. In step S86, the converted digital data value, i.e., the detected value, and a predetermined reference value are compared. If the detected value is smaller than the predetermined reference value, the detection point is moved, and the operation returns to step S84. If the detected value is value greater than or equal to reference value, the operation proceeds to a subsequent step. In step S88, the detected value is displayed on the display 22, and an indication that the detected value is the maximum value is displayed, thereby completing the optimal diagnosis point detecting method.

According to the first embodiment of the present invention, an ultrasonic generating means and an ultrasonic detecting means are used as the light generator 12 and photodetector 14, respectively. In this case, since the magnitude of the signal output according to the frequency of the detected signal, the ultrasonic detecting means detects the frequency of the reflected ultrasonic waves to discriminate a detection signal, thereby detecting the optimal diagnosis point.

Figure 2:
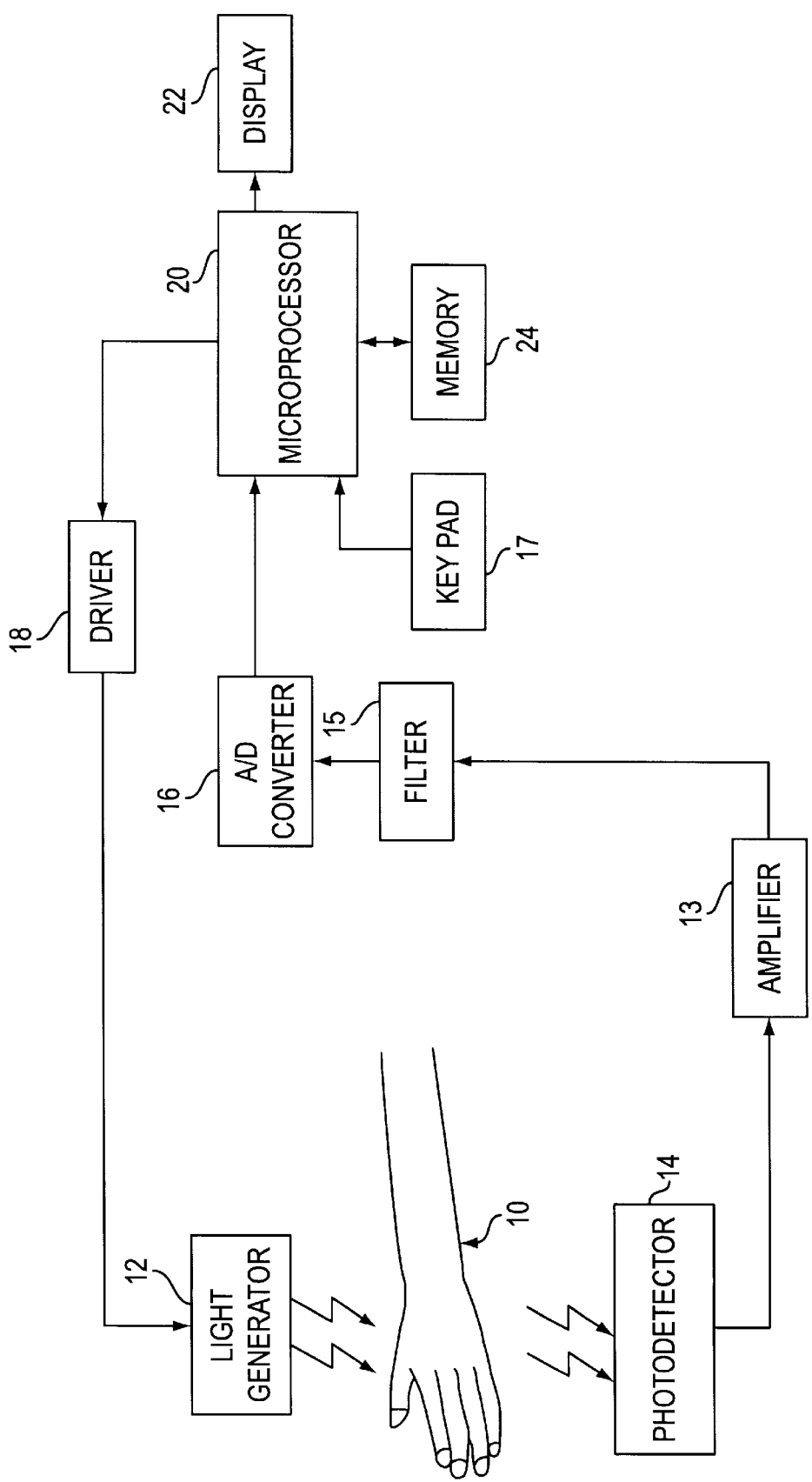
FIG. 2 is a block diagram illustrating an optimal diagnosis point detector for noninvasive diagnosis of blood constituents according to a second embodiment of the present invention.
Figure 3:
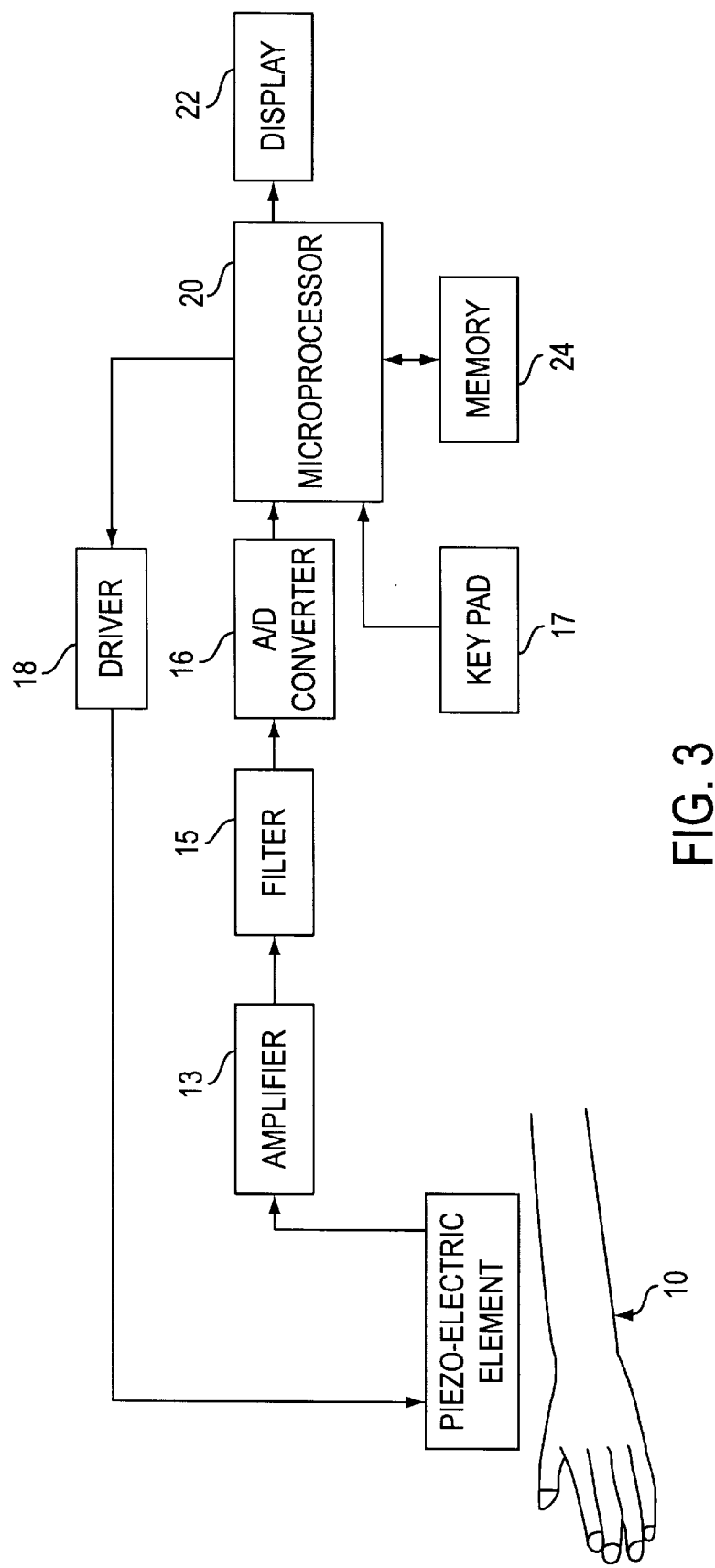
FIG. 3 is a block diagram illustrating an optimal diagnosis point detector for noninvasive diagnosis of blood constituents according to a third embodiment of the present invention.
Figure 4:
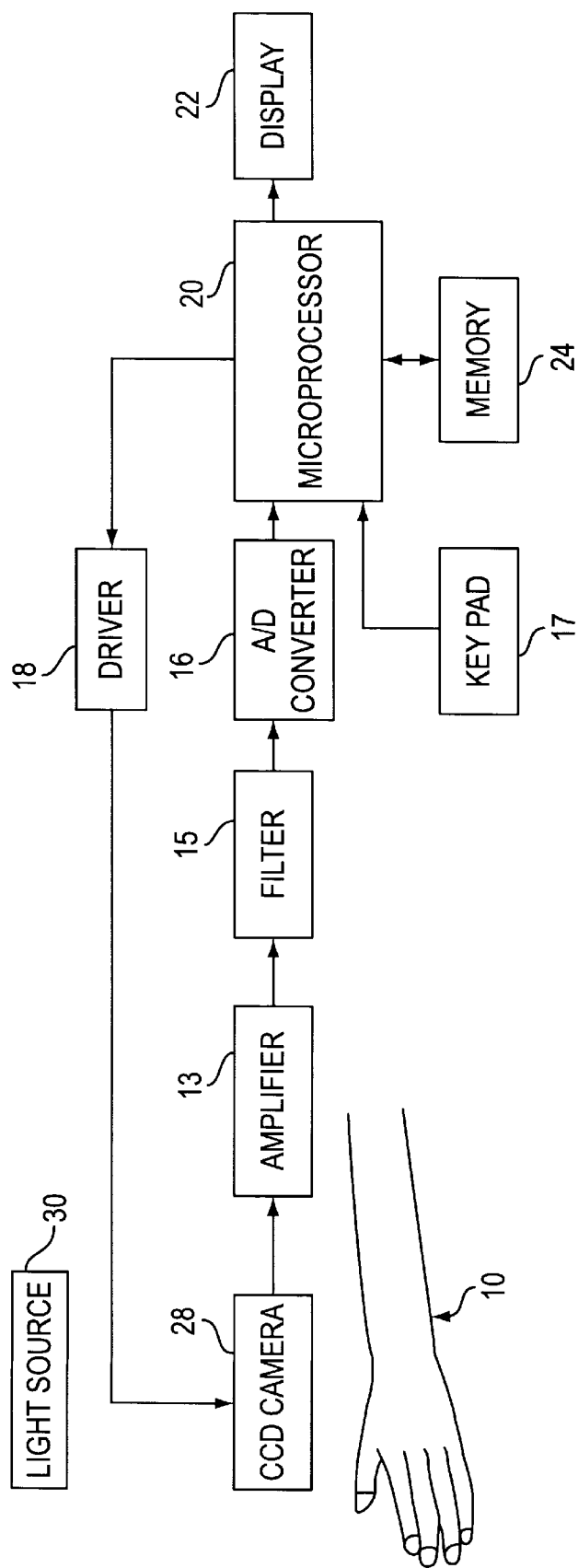
FIG. 4 is a block diagram illustrating an optimal diagnosis point detector for noninvasive diagnosis of blood constituents according to a fourth embodiment of the present invention.

FIGS. 2, 3, and 4 schematically show an optimal diagnosis point detector for noninvasive diagnosis of blood constituents according to second, third and fourth embodiments of the present invention.

Referring to FIG. 2, in the optimal diagnosis point detector for noninvasive diagnosis of blood constituents according to the second embodiment of the present invention, the photodetector 14 detects light transmitted through the portion to be diagnosed, unlike the optimal diagnosis point detector shown in FIG. 1 in which the photodetector 14 detects the reflected light. Here, the light generator 12 is preferably a flash lamp for generating pulsating light of a predetermined width or a continuous emitting bulb for emitting continuous light. Also, referring to FIG. 3, instead of the light generator 12 and photodetector 14 used in the first embodiment, a piezo-electric element 26 used in the optimal diagnosis point detector according to the third embodiment of the present invention to detect the pressure of a point where the flow of blood through a bloodstream is largest, thereby detecting a point where the detected value is maximum.

In the optimal diagnosis point detector according to the fourth embodiment of the present invention shown in FIG. 4, a charge coupled device (CCD) camera 28 is used as the detecting means. The light generated from a light source 30 is irradiated into the portion 10 to be diagnosed, and then the portion 10 to be diagnosed is photographed by the CCD camera 28, thereby detecting a point where the level of brightness in the grade scale due to a high flow in the bloodstream changes sharply to then display the detected point on the display 22. In order to conduct noninvasive diagnosis using the optimal diagnosis point detector according to the fourth embodiment of the present invention, a detector of a noninvasive diagnostic device (not shown) is positioned at the optimal diagnosis point indicated in the display 22.

Next, the operation of the noninvasive diagnosis device having the optimal diagnosis point detector for noninvasive diagnosis of blood constituents according to the present invention will be described with reference to FIGS. 7 and 8.

Figure 7:
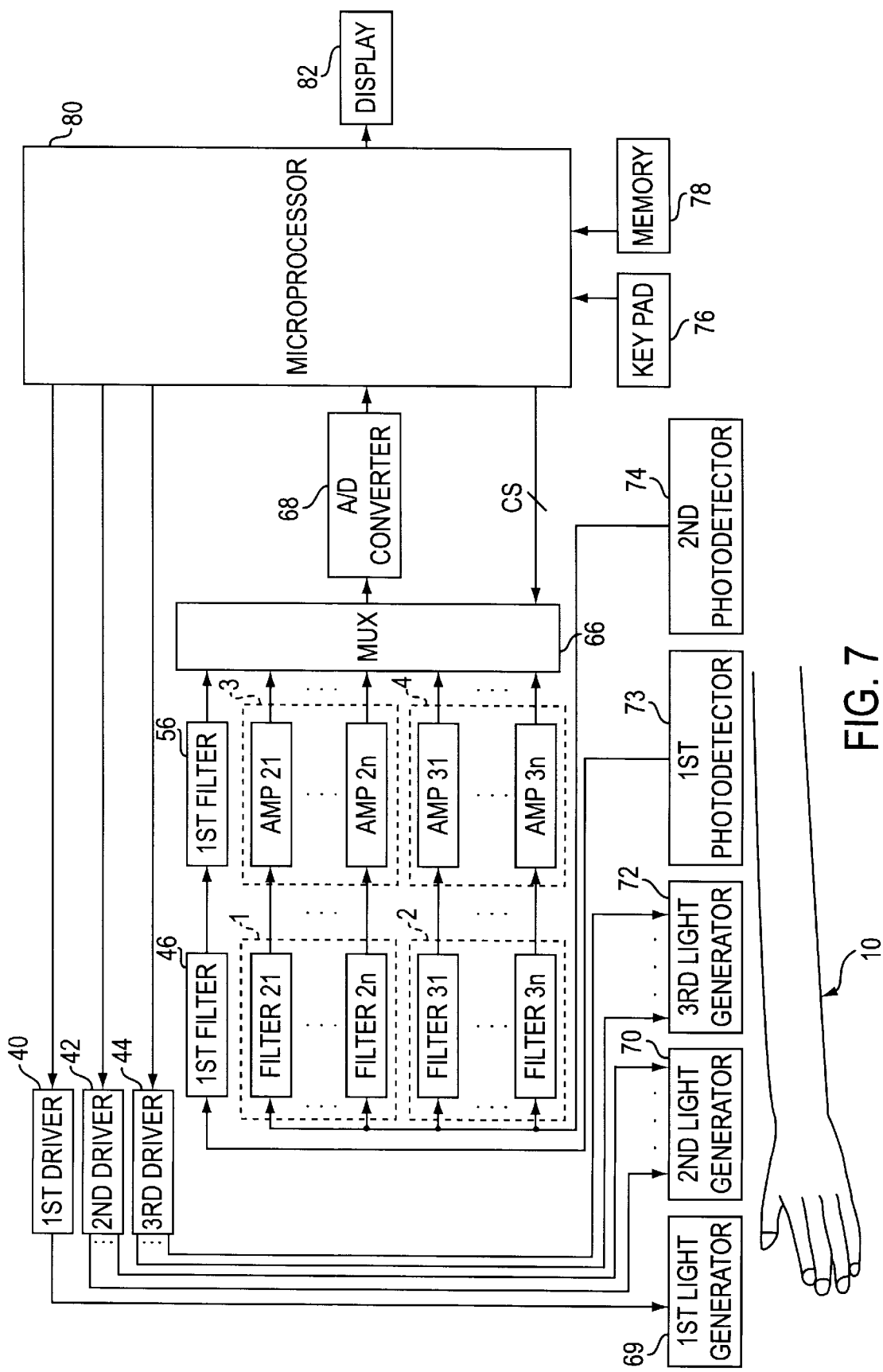
FIG. 7 is a block diagram of a noninvasive diagnostic device using the optimal diagnosis point detector for noninvasive diagnosis of blood constituents according to the present invention.
Figure 8:
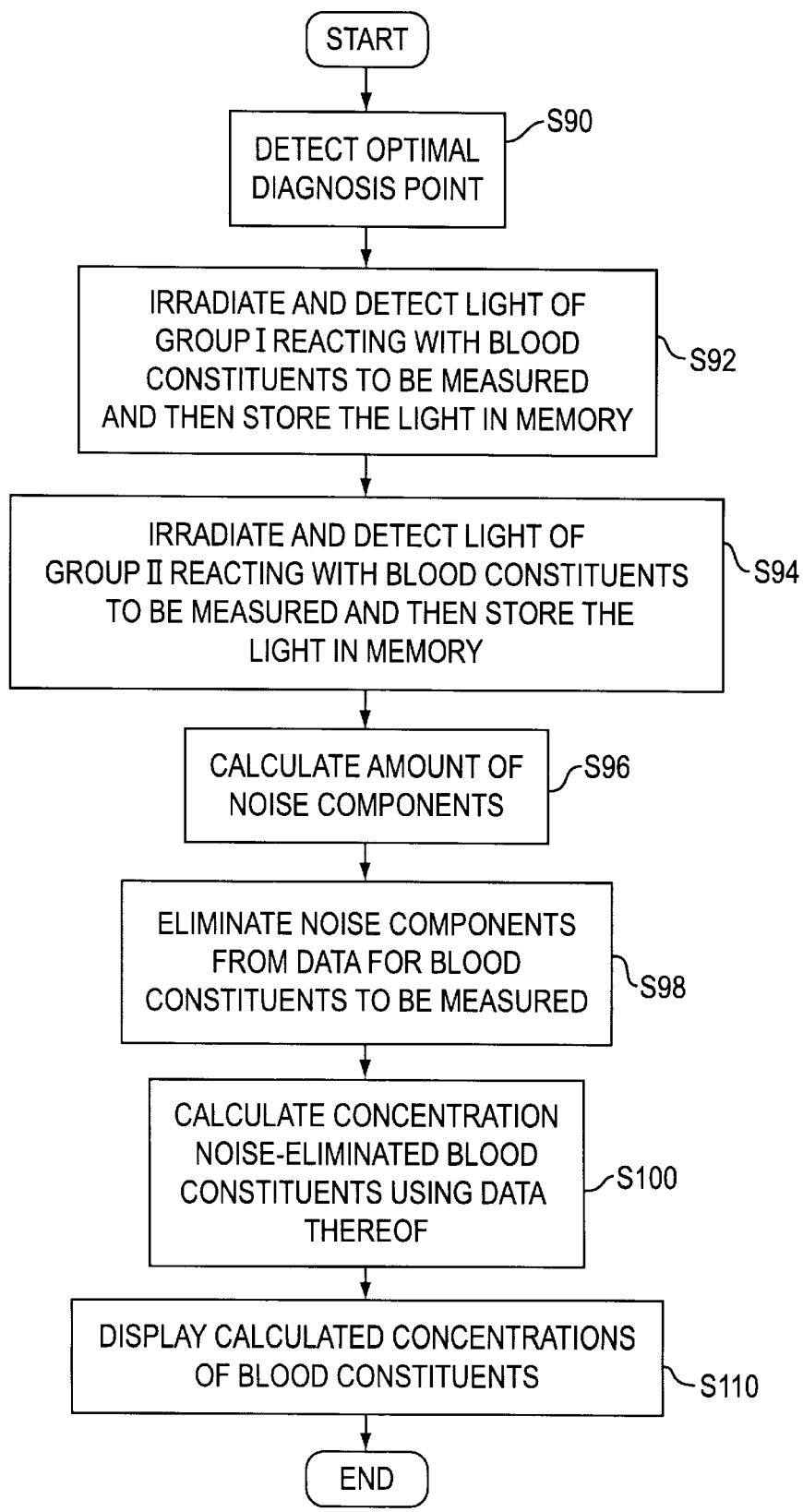
FIG. 8 is a flow chart for explaining the operation of the noninvasive diagnostic device using the optimal diagnosis point detector for noninvasive diagnosis of blood constituents shown in FIG. 7.

FIG. 7 is a block diagram of a noninvasive diagnosis device using the optimal diagnosis point detector for noninvasive diagnosis of blood constituents according to the present invention, and FIG. 8 is a flow chart for explaining the operation of the noninvasive diagnosis device using the optimal diagnosis point detector for noninvasive diagnosis of blood constituents shown in FIG. 7.

Referring to FIGS. 7 and 8, the noninvasive diagnosis device having the optimal diagnosis point detector for noninvasive diagnosis of blood constituents according to an embodiment of the present invention includes a first light generator 69 for irradiating light of a predetermined wavelength into a portion 10 of the subject to be diagnosed, a first photodetector 73 for detecting the amount of light reflected or transmitted from the subject's blood constituents, a first driver 40 for driving the first light generator 69, a first amplifier 46 for amplifying a detection signal output from the first photodetector 73, a first filter 56 for filtering an output signal of the first amplifier 46, a second light generator 70 for irradiating a plurality of light beams of different wavelengths to react to the blood constituents to be measured into a portion 10 of the subject to be diagnosed, a third light generator 72 for irradiating a plurality of light beams of different wavelengths to react to the constituents other than the blood constituents to be measured into a portion 10 of the subject to be diagnosed, a second photodetector 74 for detecting the light reflected or transmitted from the portion 10 to be diagnosed, a second driver 42 for driving the second light generator 70, a second filter 1 for filtering a signal in the range of wavelengths reacting with blood constituents to be measured among the outputs of the second photodetector 74, a third filter 2 for filtering a signal in the range of wavelengths reacting with the constituents other than blood constituents to be measured among the outputs of the second photodetector 74, a second amplifier 3 for amplifying the output of the second filter 1, a third amplifier 4 for amplifying the output of the third filter 2, a multiplexer 66 for multiplexing the outputs of the first filter 56, second and third amplifiers 3 and 4, an analog-to-digital (A/D) converter 68 for converting the output signal of the multiplexer 66 into digital data, a memory 78 in which a predetermined optimal diagnosis point detecting method and a blood constituent concentration calculating method are stored, a key pad 76 through which a user's command is input, a microprocessor 80 connected to the first, second and third drivers 40, 42 and 44, the A/D converter 68, the memory 78, and the key pad 76, for performing the optimal diagnosis point detecting method and blood constituent concentration calculating method according to the user's input command, and a display 82 connected to the microprocessor 80, for displaying a detected value, displaying an indication that the detected value is the maximum value, and displaying the calculated blood constituent concentration when the maximum detection signal is detected from the first photodetector 73.

In the aforementioned configuration, the second filter 1 includes a plurality of filters, the third filters 2 includes a plurality of filters, the second amplifier 3 includes a plurality of filters, and the third amplifier 4 includes a plurality of filters.

Next, the operation of the noninvasive diagnosis device having the above optimal diagnosis point detector for noninvasive diagnosis of blood constituents according to the present invention will be explained in view of the optimal diagnosis point detecting method and blood constituent concentration calculating method which are performed by the microprocessor 80.

Since the optimal diagnosis point detecting methods is the same as that illustrated in FIG. 5 or FIG. 6, the explanation thereof will be omitted herein. After detecting the optimal diagnosis point, the operation related to the blood constituent calculating method will be explained.

Referring to FIGS. 6, 7 and 8, in step S90, the optimal diagnosis point is detected according to the sequence flow shown in FIG. 5 or FIG. 6 using the first driver 40, the first light generator 69, the first photodetector 73, the first amplifier 46, and the first filter 56. In step S92, the second driver 42 is operated by applying a predetermined signal thereto, the second light generator 70 sequentially generates the light of Group I to react to the blood constituents to be measured by the input signal of the second driver 42 to irradiate the light of Group 1 into the portion 10 to be diagnosed, parts of the light irradiated into the portion 10 to be diagnosed are reflected to be filtered by the second filter 1 and amplified by the second amplifier 3. Then the microprocessor 80 converts the detected signal into digital data by the A/D converter 68 by applying a control signal CS to the multiplexer 66 and sequentially stores the converted data in the memory 78.

In step S94, the third driver 44 is operated by applying a predetermined signal to the third driver 44, the third light generator 72 then generates light of Group II to react to constituents other than blood constituents, e.g., skin, bone, water or fat, by the output signal of the third driver 44 to irradiate the light into the portion 10 to be diagnosed, parts of the light irradiated into the portion 10 to be diagnosed are reflected to be filtered by the second filter 1 and amplified by the third amplifier 3. Then the microprocessor 80 converts the detected signal into digital data by the A/D converter 68 by applying a control signal CS to the multiplexer and sequentially stores the converted data in the memory 78.

In step S96, the amount of noise components is calculated using the digital data for the signal reflected by reaction to the constituents other than blood constituents to be measured stored in the memory 78. In step S98, the noise component effect is minimized from the digital data for the blood constituents to be measured by subtracting a value obtained by multiplying the calculated amount of the noise components with a predetermined proportional constant from the digital data for the signal reflected by reaction to the blood constituents to be measured stored in the memory 78. As described above, the noise components are eliminated from the detected signal, thereby calculating the concentration of the blood constituents to be measured accurately.

In step S100, the accurate concentration of the noise-eliminated blood constituents to be measured is calculated using the digital data thereof. The blood constituents are accurately calculated using a graph illustrating the experimentally obtained concentration of the blood constituents to be measured and a predetermined equation. In step S110, the concentration of the blood constituents calculated in the step S100 is displayed on the display 82 to notify to the user. Here, the first, second, and third light generators 69, 70, and 72 are preferably a flash lamp for generating pulsating light of a predetermined width or a continuous emitting bulb for emitting continuous light. Specifically, when the flash lamp is used as the first, second, and third light generators 69, 70, and 72, the light generators 69, 70, and 72 generate light pulses having a very strong intensity instantaneously. Thus, the overall S/N ratio can be improved.

As described above, according the present invention, since the noninvasive diagnosis is conducted at a point where the detected value becomes the maximum value due to the maximum bloodstream quantity after detecting the point, the concentration of the subject's blood constituents can be measured accurately. Also, since a plurality of light beams are used and noise components are eliminated therefrom to minimize the noise component effect, the constituents that are very lightly concentrated in blood can be accurately measured.

What is claimed is:

1. An optimal diagnosis point detector for noninvasive diagnosis of blood constituents in a patient's bloodstream comprising:

a detecting unit for generating an input signal to irradiate a portion of the patient to be diagnosed and for detecting at least one of a predetermined signal that has passed through a portion of a patient's bloodstream to be diagnosed and a predetermined signal that has been reflected from said portion to be diagnosed, said detecting unit also for outputting an output signal representative of characteristics in the patient's bloodstream;

a driving unit for driving said detecting unit;

an amplifier for amplifying the output signal of said detecting unit;

an analog-to-digital converter for receiving a signal output from said amplifier and converting the signal output from said amplifier into a digital detected value;

a storage unit for storing a predetermined optimal diagnosis point detecting method;

a command inputting unit through which a user's command is input;

a central processing unit, connected to said driving unit, said analog-to-digital converter, said command inputting unit, and said storage unit, for performing said predetermined optimal diagnosis point detecting method stored in said storage unit according to the user's input command; and a display unit connected to said central processing unit for displaying said digital detected value and displaying an indication that said digital detected value is a maximum value when a maximum detection signal is detected from said detecting unit.

2. The optimal diagnosis point detector as claimed in claim 1, wherein said optimal diagnosis point detecting method performed by said central processing unit comprises:

a) operating said driving unit by applying a predetermined signal thereto;

b) converting the signal output from said amplifier into said digital detected value using said analog-to-digital converter;

c) comparing said digital detected value with a predetermined reference value, moving a detection point, and then returning to said step b) if said digital detected value is smaller than said predetermined reference value, and proceeding to a subsequent step if said digital detected value is greater than or equal to said predetermined reference value; and d) displaying said digital detected value on said display unit and displaying an indication that said digital detected value is a maximum value.

3. The optimal diagnosis point detector as claimed in claim 2, wherein said detecting unit includes a light generator for generating light to irradiate the light into said portion to be diagnosed, and a photodetector for detecting a light amount reflected or transmitted from said portion to be diagnosed.

4. The optimal point diagnosis detector as claimed in claim 3, wherein said light generator is at least one of a flash lamp for generating pulsating light and a continuous emitting bulb.

5. The optimal point diagnosis detector as claimed in claim 2, wherein said detecting unit includes an ultrasonic generating unit for generating an ultrasonic wave to irradiate the ultrasonic wave into said portion to be diagnosed and an ultrasonic detecting unit for detecting a frequency of the ultrasonic wave reflected from said portion to be diagnosed.

6. The optimal diagnosis point detector as claimed in claim 1, further comprising:

a filter for filtering the output signal of said amplifier between said amplifier and said analog-to-digital converter.

7. The optimal diagnosis point detector as claimed in claim 1, wherein said detecting unit includes a light generator for generating light to irradiate the light into said portion to be diagnosed, and a photodetector for detecting a light amount reflected or transmitted from said portion to be diagnosed.

8. The optimal point diagnosis detector as claimed in claim 7, wherein said light generator is at least one of a flash lamp for generating pulsating light and a continuous emitting bulb.

9. The optimal point diagnosis detector as claimed in claim 1, wherein said detecting unit includes an ultrasonic generating unit for generating an ultrasonic wave to irradiate the ultrasonic wave into said portion to be diagnosed and an ultrasonic detecting unit for detecting a frequency of the ultrasonic wave reflected from said portion to be diagnosed.

10. An optimal diagnosis point detector comprising:

a detecting unit for detecting a predetermined signal concerning bloodstream quantity from a portion of a patient to be diagnosed and for outputting an output signal representative of the bloodstream quantity;

a driving unit for driving said detecting unit;

an amplifier for amplifying the output signal of said detecting unit;

an analog-to-digital converter for receiving a signal output from said amplifier and converting the signal output from said amplifier into digital data;

a storage unit for storing a predetermined optimal diagnosis point detecting method;

a command inputting unit through which a user's command is input;

a central processing unit, connected to said driving unit, said analog-to-digital converter, said command inputting unit, and said storage unit, for performing said predetermined optimal diagnosis point detecting method stored in said storage unit according to the user's input command; and a display unit connected to said central processing unit for displaying a detected value and displaying an indication that said detected value is a maximum value when a maximum detection signal is detected from said detecting unit, wherein said optimal diagnosis point detecting method performed by said central processing unit includes:

a) operating said driving unit by applying a predetermined signal thereto;

b) converting the signal output from said amplifier into a digital detected value using said analog-to-digital converting unit;

c) comparing said digital detected value with a predetermined reference value, moving a detection point, and then returning to said step b) if said digital detected value is smaller than said predetermined reference value, and proceeding to a subsequent step if said digital detected value is greater than or equal to said predetermined reference value;

d) replacing said reference value with said digital detected value;

e) displaying said digital detected value on said display unit;

f) determining whether a number of detections is greater than or equal to a predetermined number of times, moving a detection point, and then returning to said step b) if said number of detections is smaller than said predetermined number, and proceeding to a subsequent step if said number of detections is greater than or equal to said predetermined number; and g) displaying said digital detected value on said display unit and displaying an indication that said digital detected value is a maximum value.

11. The optimal diagnosis point detector as claimed in claim 10, wherein said detecting unit is a piezoelectric element for detecting variations in pressure of said portion to be diagnosed, where the pressure changes according to the flow of the bloodstream.

12. The optimal diagnosis point detector as claimed in claim 10, wherein said detecting unit is a charge-coupled device (CCD) camera, and said optimal diagnosis point detecting method is performed by photographing said portion to be diagnosed with said CCD camera and then detecting a portion where a level of brightness in a grade scale changes sharply due to a large flow of blood in a bloodstream at said photographed portion.

13. A method of performing optimal diagnosis point detection for noninvasive diagnosis of blood constituents in a patient's bloodstream, comprising the steps of:

(a) providing a detecting unit for generating an input signal to irradiate a portion of the patient to be diagnosed and for detecting at least one of (i) a predetermined signal that has passed through a portion of the patient's bloodstream to be diagnosed and (ii) a predetermined signal that has been reflected from a portion of the patient's bloodstream to be diagnosed and for outputting an output signal representative of the constituents in the patient's bloodstream, a drive apparatus for driving the detector, an amplifier for amplifying an output signal of the detecting unit, an analog-to-digital converter, and a display;

(b) operating the drive apparatus to drive the detecting unit;

(c) detecting a signal via the detecting unit and amplifying the detected signal in the amplifier;

(d) converting a signal output from the amplifier into a digital detected value using the analog-to-digital converter;

(e) comparing the digital detected value with a predetermined reference value, moving a detection point, and then returning to step (c) if the digital detected value is smaller than the predetermined reference value, and proceeding to a subsequent step if the digital detected value is greater than or equal to the predetermined reference value; and (f) displaying the digital detected value on the display and displaying an indication that the digital detected value is a maximum value.

14. A method as claimed in claim 13, further comprising the steps of:

(g) providing a first light emitter for generating a first plurality of beams having different wavelengths to react to blood constituents in a portion to be diagnosed, a second light emitter for generating a second plurality of beams having different wavelengths to react to constituents other than blood constituents in the portion to be diagnosed, a second detector for detecting reflected or transmitted light from the portion to be diagnosed, a second drive apparatus, a plurality of first filters for filtering outputs of the second detector at frequency bands of respective beams generated by the first light emitter, a plurality of second filters for filtering outputs of the second detector at frequency bands of respective beams generated by the second light emitter, a second amplifier, and a third amplifier;

(h) operating the second drive apparatus by applying a predetermined signal thereto when an optimal diagnosis point is detected by steps (a) through (f);

(i) converting a plurality of signals amplified by the second amplifier into digital detected signals and storing the digital detected signals as a first set;

(j) converting a plurality of signals amplified by the third amplifier into digital detected signals and storing the digital detected signals as a second set;

(k) calculating an amount of noise components other than components to be measured using a value converted into digital data via the plurality of second filters;

(l) eliminating noise components from the data of blood constituents to be measured by subtracting a value obtained by reflecting a scale constant on the noise component amount calculated in step (k) from a value converted into digital data via the plurality of first filters to obtain a value of the noise-eliminated blood constituents;

(m) calculating a concentration of blood constituents to be measured using the value of the noise-eliminated blood constituents; and (n) displaying the calculated concentration on the display.

15. A method of performing optimal diagnosis point detection for noninvasive diagnosis of blood constituents, comprising the steps of:

(a) providing a detector for detecting a predetermined signal concerning bloodstream quantity from a portion of a patient to be diagnosed, a drive apparatus for driving the detecting unit, an amplifier for amplifying an output signal of the detecting unit, an analog-to-digital converter, and a display;

(b) operating the drive apparatus to drive the detecting unit;

(c) detecting a signal via the detecting unit and amplifying the detected signal in the amplifier;

(d) converting a signal output from the amplifier into a digital detected value using the analog-to-digital converter;

(e) comparing the digital detected value with a predetermined reference value, moving a detection point, and then returning to step (c) if the digital detected value is smaller than the predetermined reference value, and proceeding to a subsequent step if the digital detected value is greater than or equal to the predetermined reference value;

(f) replacing the reference value with the digital detected value;

(g) displaying the digital detected value on the display;

(h) determining whether a number of detections is greater than or equal to a predetermined number, moving a detection point, and then returning to step (c) if the number of detections is smaller than the predetermined number, and proceeding to step (i) if the number of detections is greater than or equal to the predetermined number; and (i) displaying the digital detected value on the display and displaying an indication that the digital detected value is a maximum value.

16. A method as claimed in claim 15, further comprising the steps of:

(j) providing a first light emitter for generating a first plurality of beams having different wavelengths to react to blood constituents in a portion to be diagnosed, a second light emitter for generating a second plurality of beams having different wavelengths to react to constituents other than blood constituents in the portion to be diagnosed, a second detector for detecting reflected or transmitted light from the portion to be diagnosed, a second drive apparatus, a plurality of first filters for filtering outputs of the second detector at frequency bands of respective beams generated by the first light emitter, a plurality of second filters for filtering outputs of the second detector at frequency bands of respective beams generated by the second light emitter, a second amplifier, and a third amplifier;

(k) after step (f), operating the second drive apparatus by applying a predetermined signal thereto when an optimal diagnosis point is detected by steps (a)–(i);

(l) converting a plurality of signals amplified by the second amplifier into digital detected signals and storing the digital detected signals as a first set;

(m) converting a plurality of signals amplified by the third amplifier into digital detected signals and storing the digital detected signals as a second set;

(n) calculating an amount of noise components other than components to be measured using a value converted into digital data via the plurality of second filters;

(o) eliminating noise components from the data of blood constituents to be measured by subtracting a value obtained by reflecting a scale constant on the noise component amount calculated in step (n) from a value converted into digital data via the plurality of first filters to obtain a value of the noise-eliminated blood constituents;

(p) calculating a concentration of blood constituents to be measured using the value of the noise-eliminated blood constituents; and (q) displaying the calculated concentration on the display.

17. A noninvasive diagnostic device, comprising:

first detecting unit for generating an input signal to irradiate a portion of the patient to be diagnosed and for detecting at least one of a predetermined signal that has passed through a patient's bloodstream to be diagnosed and a predetermined signal that has been reflected from said portion to be diagnosed, said first detecting unit also for outputting an output signal representative of the blood constituents in the patient's bloodstream;

first driving unit for driving said first detecting unit;

first amplifying unit for amplifying an output signal of said first detecting unit;

first light emitting unit for emitting a first plurality of beams having different wavelengths to react to blood constituents to be measured to irradiate the first plurality of beams into said portion to be diagnosed;

second light emitting unit for emitting a second plurality of beams having different wavelengths to react to the constituents other than blood constituents to be measured to irradiate the second plurality of beams into said portion to be diagnosed;

second detecting unit for detecting reflected or transmitted light from said portion to be diagnosed after the first and second plurality of beams are irradiated;

second driving unit for driving said first light emitting unit;

third driving unit for driving said second light emitting unit;

first filtering unit having a first plurality of filters for filtering respective outputs of said second detecting unit at frequency bands of respective beams emitted by said first light emitting unit;

second filtering unit having a second plurality of filters for filtering respective outputs of said second detecting unit at frequency bands of respective beams emitted by said second light emitting unit;

second amplifying unit having a first plurality of amplifiers for amplifying respective outputs of said first filtering unit;

third amplifying unit having a second plurality of amplifiers for amplifying respective outputs of said first filtering unit;

multiplexing unit for multiplexing outputs of said first, second, and third amplifying units;

analog-to-digital converter for converting an output signal of said multiplexing unit into digital data;

storage unit for storing a predetermined optimal diagnosis point detecting method and a blood constituent concentration calculation method;

command inputting unit through which a user's command is input;

central processing unit, connected to said first, second, and third driving units, said analog-to-digital converter, said storage unit, and said command inputting unit, for performing said optimal diagnosis point detecting method and said blood constituent concentration calculating method stored in said storage unit according to the user's input command; and display unit connected to said central processing unit for displaying a detected value, displaying an indication that said detected value is a maximum value when a maximum detection signal is detected from said first detecting unit, and displaying a calculated blood constituent concentration.

18. The noninvasive diagnostic device of claim 17, wherein said optimal diagnosis point detecting method and said blood constituent concentration calculating method performed by said central processing unit comprise:

a) operating said first driving unit by applying a predetermined signal thereto;

b) converting a signal output from said first amplifying unit into a digital detected value using said analog-to-digital converter by applying a control signal to said multiplexing unit and inputting the signal output from said first amplifying unit into said analog-to-digital converter;

c) comparing said digital detected value with a predetermined reference value, moving a detection point, and then returning to said step b) if said digital detected value is smaller than said predetermined reference value, and proceeding to a subsequent step if said digital detected value is greater than or equal to said predetermined reference value;

d) displaying said digital detected value on said display unit and displaying an indication that said digital detected value is a maximum value;

e) operating said second driving unit by applying a predetermined signal thereto when an optimal diagnosis point is detected by said steps a) through d);

f) inputting a plurality of signals amplified by said second amplifying unit into said analog-to-digital converter by applying a control signal into said multiplexing means, converting the plurality of signals amplified by said second amplifying unit into digital data, and storing the converted data in said storage unit;

g) inputting a plurality of signals amplified by said third amplifying unit into said analog-to-digital converter by applying a control signal into said multiplexing unit, converting the plurality of signals amplified by said third amplifying unit into digital data, and storing the converted data in said storage unit;

h) calculating an amount of noise components other than components to be measured using a value converted into digital data via said second filtering unit;

i) eliminating noise components from the data of blood constituents to be measured by subtracting a value obtained by reflecting a scale constant on the noise component amount calculated in said step h) from said converted value via said first filtering unit to obtain a value of the noise-eliminated blood constituents;

j) calculating a concentration of blood constituents to be measured using the value of the noise-eliminated blood constituents; and k) displaying said calculated concentration on said display unit.

19. The noninvasive diagnostic device of claim 17, wherein said optimal diagnosis point detecting method and said blood constituent concentration calculating method performed by said central processing unit comprise:

a) operating said first driving unit by applying a predetermined signal thereto;

b) converting a signal output from said first amplifying unit into a digital detected value using said analog-to-digital converter by applying a control signal to said multiplexing unit and inputting the signal output from said first amplifying unit into said analog-to-digital converter;

c) comparing said digital detected value with a predetermined reference value, moving a detection point, and then returning to said step b) if said digital detected value is smaller than said predetermined reference value, and proceeding to a subsequent step if said digital detected value is greater than or equal to said predetermined reference value;

d) replacing said reference value with said digital detected value;

e) displaying said digital detected value on said display unit;

f) determining whether a number of detections is greater than or equal to a predetermined number, moving a detection point, and then returning to said step b) if said number of detections is smaller than said predetermined number, and proceeding to a subsequent step if said number of detections is greater than or equal to said predetermined number;

g) displaying said digital detected value and displaying an indication that said digital detected value is a maximum value;

h) operating said second driving unit by applying a predetermined signal thereto when an optimal diagnosis point is detected by said steps b) through g);

i) sequentially inputting a plurality of signals amplified by said second amplifying unit into said analog-to-digital converter by applying a control signal into said multiplexing unit, converting the plurality of signals amplified by said second amplifying unit into digital data, and storing the converted data in said storage unit;

j) inputting a plurality of signals amplified by said third amplifying unit into said analog-to-digital converter by applying a control signal into said multiplexing unit, converting the plurality of signals amplified by said third amplifying unit into digital data, and storing the converted data in said storage unit;

k) calculating an amount of noise components other than components to be measured using a value converted into digital data via said second filtering unit;

l) eliminating noise components from the data of blood constituents to be measured by subtracting a value obtained by reflecting a scale constant on the noise component amount calculated in said step k) from said converted value via said first filtering unit to obtain a value of the noise-eliminated blood constituents;

m) calculating a concentration of blood constituents to be measured using the value of the noise-eliminated blood constituents; and n) displaying said calculated concentration on said display unit.

20. The noninvasive diagnostic device of claim 17, wherein said first detecting unit comprises a light generating unit to irradiate the light into said portion to be diagnosed, and a photodetector for detecting a light amount reflected or transmitted from said portion to be diagnosed.

21. The noninvasive diagnostic device of claim 20, wherein said light generating unit is at least one of a flash lamp for generating pulsating light and a continuous emitting bulb.

22. The noninvasive diagnostic device of claim 17, wherein each of said first and second light emitting units is at least one of a laser diode, an emitting diode, and a lamp for generating the light of wide-band frequency.

23. The noninvasive diagnostic device of claim 17, wherein said first and second light emitting units are at least one of a flash lamp for generating pulsating light and a continuous emitting bulb for emitting continuous light.

* * * * *